United States Patent
Stewart et al.

(10) Patent No.: US 12,076,162 B2
(45) Date of Patent: Sep. 3, 2024

(54) SYSTEMS AND METHODS FOR DETECTING EDEMA BY FUSING HYPERSPECTRAL AND VISIBLE IMAGE

(71) Applicant: CHEMIMAGE CORPORATION, Pittsburgh, PA (US)

(72) Inventors: Shona Stewart, Pittsburgh, PA (US); J. Christopher Post, Mars, PA (US); Patrick Treado, Pittsburgh, PA (US); Jeffrey Cohen, Pittsburgh, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 1249 days.

(21) Appl. No.: 16/315,390

(22) PCT Filed: Jul. 6, 2017

(86) PCT No.: PCT/US2017/040910
§ 371 (c)(1),
(2) Date: Jan. 4, 2019

(87) PCT Pub. No.: WO2018/009670
PCT Pub. Date: Jan. 11, 2018

(65) Prior Publication Data
US 2019/0231260 A1    Aug. 1, 2019

Related U.S. Application Data

(60) Provisional application No. 62/359,030, filed on Jul. 6, 2016.

(51) Int. Cl.
*A61B 5/00* (2006.01)
*A61B 5/05* (2021.01)
(Continued)

(52) U.S. Cl.
CPC ............ *A61B 5/4878* (2013.01); *A61B 5/05* (2013.01); *A61B 5/1455* (2013.01);
(Continued)

(58) Field of Classification Search
CPC ...... A61B 5/4878; A61B 5/1455; G02F 1/216
See application file for complete search history.

(56) References Cited

U.S. PATENT DOCUMENTS

| | | | |
|---|---|---|---|
| 6,332,091 | B1 | 12/2001 | Burns et al. |
| 6,640,130 | B1 * | 10/2003 | Freeman ............... A61B 5/0073 382/128 |

(Continued)

FOREIGN PATENT DOCUMENTS

| | | |
|---|---|---|
| CN | 101744611 A | 6/2010 |
| CN | 103622674 B | 3/2015 |

(Continued)

OTHER PUBLICATIONS

Kollias et al (Optical Non-Invasive Approaches to Diagnosis of Skin Diseases), Optical Diagnostics in Dermatology, vol. 7, No. 1 Dec. 2002 (Year: 2002).*

(Continued)

*Primary Examiner* — Serkan Akar
(74) *Attorney, Agent, or Firm* — DLA Piper LLP (US)

(57) ABSTRACT

System and method for detecting and monitoring edema in a patient are described. Initially, a patient's tissue is irradiated with light by a light source. A detector collects reflected light from the patient's tissue and generates data associated with the reflected light. A processing device receives the data and reflected light and calculates an intensity of the reflected light. The processing device then determined, based upon the intensity of the reflected light, whether the patient's tissue exhibits any symptoms of edema. Additionally, the processing device can compare a current intensity of the (Continued)

reflected light against historic information to monitor for any changes in a patient's edema level or severity.

11 Claims, 6 Drawing Sheets

(51) Int. Cl.
  *A61B 5/1455* (2006.01)
  *G02F 1/1335* (2006.01)
  *G02F 1/21* (2006.01)
  *G16H 50/30* (2018.01)
(52) U.S. Cl.
  CPC .......... *A61B 5/4842* (2013.01); *A61B 5/4869* (2013.01); *G02F 1/1335* (2013.01); *G02F 1/216* (2013.01); *G16H 50/30* (2018.01)

(56) References Cited

U.S. PATENT DOCUMENTS

| | | | |
|---|---|---|---|
| 7,577,469 | B1 | 8/2009 | Aronowitz et al. |
| 2001/0052979 | A1 | 12/2001 | Treado et al. |
| 2002/0193689 | A1 | 12/2002 | Bernstein et al. |
| 2003/0060693 | A1 | 3/2003 | Monfre et al. |
| 2005/0065813 | A1 | 3/2005 | Mishelevich et al. |
| 2006/0247514 | A1* | 11/2006 | Panasyuk .................. G01J 3/10 600/410 |
| 2006/0250613 | A1 | 11/2006 | Demuth et al. |
| 2008/0081975 | A1 | 4/2008 | Agashe et al. |
| 2008/0192246 | A1 | 8/2008 | Neiss et al. |
| 2008/0298402 | A1* | 12/2008 | Rossi .................. H01S 5/02325 372/20 |
| 2009/0082637 | A1 | 3/2009 | Galperin |
| 2010/0100395 | A1 | 4/2010 | Prasad et al. |
| 2010/0106210 | A1 | 4/2010 | Hedberg et al. |
| 2014/0032242 | A1 | 1/2014 | LaBorde et al. |
| 2014/0183366 | A1 | 7/2014 | Cole |
| 2014/0231626 | A1 | 8/2014 | Nelson et al. |
| 2014/0253921 | A1 | 9/2014 | Chen |
| 2014/0323822 | A1 | 10/2014 | Addison et al. |
| 2015/0044098 | A1* | 2/2015 | Smart .................. A61B 5/0084 422/82.05 |
| 2016/0004820 | A1 | 1/2016 | Moore |
| 2016/0042513 | A1* | 2/2016 | Yudovsky ............... G06T 7/337 382/128 |
| 2016/0140316 | A1 | 5/2016 | Spiegel et al. |
| 2016/0370228 | A1 | 12/2016 | Tok et al. |
| 2017/0071510 | A1 | 3/2017 | Delbeke et al. |
| 2018/0188516 | A1* | 7/2018 | Engelhardt .......... G02B 27/283 |
| 2019/0231260 | A1 | 8/2019 | Stewart et al. |

FOREIGN PATENT DOCUMENTS

| | | |
|---|---|---|
| CN | 104757949 A | 7/2015 |
| CN | 108968922 A | 12/2018 |
| WO | 2007061754 A1 | 5/2007 |
| WO | 2007088382 A1 | 8/2007 |

OTHER PUBLICATIONS

Stamatas et al., "In Vivo Monitoring of Cutaneous Edema Using Spectral Imaging in the Visible and Near Infrared," Journal of Investigative Dermatology (May 4, 2006) vol. 126, pp. 1753-1760.
International Search Report and Written Opinion for PCT/US2017/040910 dated Sep. 11, 2017.
Morris et al. "Liquid Crystal Tunable Filter Raman Chemical Imaging" 1996, Applied Spectroscopy 50(6):805-811.
Leitz et al. "Germanium CCDs for Large-format SWIR and X-ray Imaging" May 25, 2017, JINST 12 C05014, 12 pages.

* cited by examiner

SYSTEMS AND METHODS FOR DETECTING EDEMA BY FUSING HYPERSPECTRAL AND VISIBLE IMAGE

CROSS REFERENCE TO RELATED APPLICATIONS

This application is a U.S. national stage filing under 35 U.S.C. § 371 of International PCT Application No. PCT/US2017/040910, filed Jul. 6, 2017, which claims priority to and benefit of U.S. Provisional Patent Application No. 62/359,030 filed Jul. 6, 2016, entitled "SYSTEMS AND METHODS FOR DETECTING EDEMA," the content of which are incorporated herein by reference in their entireties.

TECHNICAL FIELD

The present disclosure is directed to systems and methods for non-invasive detection of a patient's health condition. More specifically, the present disclosure is directed to non-invasive detection of edema in a patient.

BACKGROUND

Edema is a symptom of numerous diseases and medical conditions such as: heart disease including, for example, congestive heart failure; liver disease including, for example, cirrhosis; blood clots or tumors that obstruct the flow of blood or lymph fluid; allergic reactions; low albumin; kidney disease; pregnancy; adverse reaction to medications; and other similar medical conditions. The edema associated with these conditions is typically observed in extremities such as limbs, particularly in the hands, feet, ankles, and calves. In some cases, edema can be detected in the abdomen or at a location of inflammation during, for example, an allergic reaction. Edema can also occur after exercise and can be symptomatic of exertion.

In the clinical setting, detection of the severity of peripheral edema is an important factor in determining treatment options for difficult and often life-threatening conditions. For example, heart failure is the leading cause of hospitalization in people older than 65 and accounts for more hospital admissions than all forms of cancer combined. Of those patients admitted and treated for heart failure, nearly 25% of patients are readmitted within 30 days of discharge. Readmission is often necessary because diuretics prescribed for heart failure patients can require frequent adjustments. When dosing is missed or adjustments to drug levels are not monitored, buildup of edema is one of the first indicators that modifications may need to be made to a patient's treatment regimen. Over time, buildup of edema can lead to a life-threatening condition.

An estimated two-thirds of readmissions are triggered by potentially remediable factors. For example, various factors such as poor discharge planning, nonadherence to recommendations regarding diet and medical treatment, inadequate follow-up, poor social supports, and delays in seeking medical attention can be factors in patient readmissions.

Currently, clinicians have various techniques for monitoring a patient following discharge. For example, a clinician can schedule regular follow-up appointments, track a patient's exercise tolerance and symptoms, monitor a patient's electrolyte levels, monitor a patient for medicinal side effects, and prescribe a tele-monitoring regimen to the patient including, for example, monitoring blood pressure, heart rate, body weight, and other related patient health parameters.

However, recent studies have shown that current tele-monitoring techniques related to monitoring of, for example, weight and various vital signs in heart failure patients as an adjunct to routine care has no significant incremental impact on morbidity and mortality.

SUMMARY

A system for detecting edema in a patient is described herein. The system includes a light source configured to irradiate a patient's tissue with light, a detector configured to collect reflected light from the patient's tissue and generate data associated with the reflected light, and a processing device operably connected to the detector. The processing device is configured to receive the data associated with the reflected light, calculate the intensity of the reflected light, and determine whether the patient's tissue exhibits symptoms of edema.

In some implementations of the above system, the processing device is further configured to determine a control measurement for a control sample. In some examples, the processing device is further configured to compare the calculated intensity of the reflected light against the control measurement, and determine an edema score for the patient, wherein the edema score represents at least one of whether the patient has edema and a severity of the patient's edema.

In some implementations of the above system, the system further includes at least one filter configured to filter the reflected light. In some examples, the at least one filter is a tunable filter configured to filter the reflected light a specific wavelength range. In some examples, the at least one filter is at least one of a shortwave infrared tunable filter, a Fabry Perot tunable filter, a multi-conjugate crystal tunable filter, and a conformal filter.

In some implementations of the above system, the system further includes plurality of tunable filters. In some examples, the plurality of tunable filters are configured to filter the reflected light to wavelength ranges of at least one of 900 nm to 1100 nm, 1150 nm to 1300 nm, and 1400 nm to 1550 nm.

In some implementations of the above system, the light source includes at least one of a laser illumination source, a broadband light source, and an ambient light source.

In some implementations of the above system, the detector includes at least one of a charge-coupled device detector, a complementary metal-oxide semiconductor detector, an indium gallium arsenide detector, and a focal plane array detector.

In some implementations of the above system, the processor is further configured to fuse intensity data from two or more imaging modalities. In some examples, the two or more imaging modalities include a visible image, a hyperspectral image, a shortwave infrared hyperspectral image, a medium-wavelength infrared hyperspectral image, a long-wavelength infrared hyperspectral image, and combinations thereof.

In some implementations of the above system, the system further includes at least one display device operably connected to the processing device and configured to display one or more images received from the processing device, the one or more images representative of the patient's tissue.

A method for detecting edema in a patient is also described herein. The method includes irradiating, by a light source, a patient's tissue with light; collecting, by a detector, reflected light from the patient's tissue; generating, by the detector, data associated with the reflected light; receiving, by a processing device operably connected to the detector, the reflected light; calculating, by the processing device, the intensity of the reflected light; and determining, by the processing device, whether the patient's tissue exhibits symptoms of edema.

In some implementations of the above method, the method further includes determining, by the processing device, a control measurement for a control sample. In some examples, the method further includes comparing, by the processing device, the calculated intensity of the reflected light against the control measurement, and determining, by the processing device, an edema score for the patient, wherein the edema score represents at least one of whether the patient has edema and a severity of the patient's edema.

In some implementations of the above method, the method further includes filtering, by at least one filter, the reflected light. In some examples, the at least one filter is a tunable filter configured to filter the reflected light within a specific wavelength range. In some examples, the at least one filter is at least one of a shortwave infrared tunable filter, a Fabry Perot tunable filter, a multi-conjugate crystal tunable filter, and a conformal filter.

In some implementations of the above method, the method further includes filtering, by a plurality of filters, the reflected light to wavelength ranges of at least one of 900 nm to 1100 nm, 1150 nm to 1300 nm, and 1400 nm to 1550 nm.

In some implementations of the above method, the light source includes at least one of a laser illumination source, a broadband light source, and an ambient light source.

In some implementations of the above method, the detector includes at least one of a charge-coupled device detector, a complementary metal-oxide semiconductor detector, an indium gallium arsenide detector, and a focal plane array detector.

In some implementations of the above method, the method further includes fusing, by the processing device, intensity data from two or more imaging modalities. In some examples, the two or more imaging modalities include a visible image, a hyperspectral image, a shortwave infrared hyperspectral image, a medium-wavelength infrared hyperspectral image, a long-wavelength infrared hyperspectral image, and combinations thereof.

In some implementations of the above method, the method further includes displaying, by at least one display device operably connected to the processing device, one or more images received from the processing device, the one or more images representative of the patient's tissue.

A method for monitoring edema in a patient is also described herein. The method for monitoring edema includes irradiating, by a light source, a patient's tissue with light; collecting, by a detector, reflected light from the patient's tissue; generating, by the detector, data associated with the reflected light; receiving, by a processing device operably connected to the detector, the reflected light; calculating, by the processing device, the intensity of the reflected light; comparing, by the processing device, the intensity of the reflected light to a control measurement to determine a current edema score; and determining a change in an edema level for the patient based upon a comparison of the current edema score and previously collected edema information.

In some implementations of the above method, the method for monitoring edema further includes determining, by the processing device, the previously collected edema information.

In some implementations of the above method, the method for monitoring edema further includes determining, by the processing device, the control measurement for a control sample.

In some implementations of the above method, the method for monitoring edema further includes displaying, by at least one display device operably connected to the processing device, one or more images received from the processing device, the one or more images representative of the patient's tissue.

DESCRIPTION OF FIGURES

Aspects, features, benefits and advantages of the embodiments described herein will be apparent with regard to the following description, appended claims, and accompanying drawings where:

DETAILED DESCRIPTION

Figure 1:
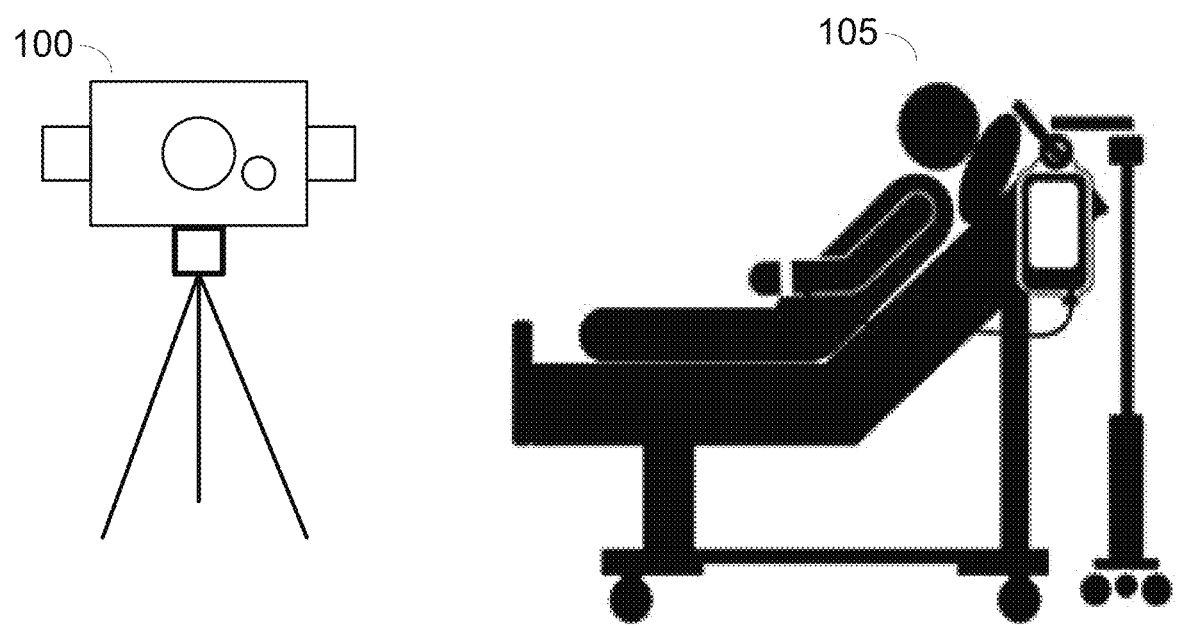
FIG. 1 depicts a sample environment where an imaging system can be used to measure fluid content in a patient's tissue in accordance with one or more embodiments of the present disclosure.

This disclosure is not limited to the particular systems, devices and methods described, as these may vary. The terminology used in the description is for the purpose of describing the particular versions or embodiments only and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The present disclosure is directed to systems and methods for detecting edema. More specifically, the present disclosure is directed to systems and methods for the non-invasive detection of edema that offers the potential to aid in ongoing monitoring of a patient's fluid retention, thereby providing clinicians with an objective method of determining edema levels to guide treatment for a variety of disease states.

The "subject" of various embodiments is generally a mammal and in certain embodiments may be a human. The subject can be healthy, known to have one or more health conditions, or suspected of having one or more health conditions. In an embodiment, tissue of the patient can be irradiated to determine an edema level. The irradiated tissue can be any tissue of the subject, and, in particular embodiments, the tissue can be tissue associated with the patient's limbs, hands, feet, ankles, calves, abdomen, a location of inflammation, or combinations thereof during practice of the method described above. In certain implementations, the irradiated tissue can be any exposed body tissue, including, for example, the patient's face in addition to the locations listed above.

The "control" of various embodiments can be obtained by collecting reflected light from unaffected tissue of the subject such as, for example, tissue of the upper arm, thigh, or back, or a "control" can be obtained from an unaffected subject or collection of subjects. For example, in some embodiments, control measurements may be an average absorbance obtained from limbs, hands, feet, ankles, calves, abdomen, or combinations thereof from numerous unaffected subjects.

In one or more implementations, methods and related processes for detecting edema as described herein generally include irradiating tissue of a subject with light, collecting reflected light of wavelengths about 900 nm to about 1100 nm, about 1150 nm to about 1300 nm, about 1400 nm to about 1550 nm, or combinations thereof, calculating an intensity of the reflected light, and comparing the intensity of reflected light to a control such as normal tissue or a baseline intensity for normal tissue. In some examples, edema can be detected based on an increase in absorbed light at these wavelengths compared to a patient's control measurements. In some implementations, systems for detecting edema as described herein can include a light source, an image detector, and a processor configured to compare intensity of reflected light of wave lengths about 900 nm to about 1100 nm, about 1150 nm to about 1300 nm, about 1400 nm to about 1550 nm, or combinations thereof, with a control such as normal tissue or a baseline for normal tissue.

It should be noted that the above wavelength ranges are provided by way of example only. In certain implementations, the collected wavelengths can vary depending upon the type of sensor used. For example, when using a silicon sensor configured to detect reflected light in, for example, near-infrared (NIR) wavelengths, the detector can be configured to collect light of wavelengths about 700 nm to 1100 nm.

In some examples, the method may further include processing calculated light intensity data. For example, in some embodiments, the methods may include the steps of fusing intensity data from two or more imaging modalities such as, for example, a visible image, a hyperspectral image, a shortwave infrared (SWIR) hyperspectral image, a medium-wavelength infrared (MWIR) hyperspectral image, a long-wavelength infrared (LWIR) hyperspectral image, and the like and combinations thereof. Such fusing can be accomplished by applying a fusion algorithm as is known in the art.

FIG. 1 illustrates a sample environment where a patient may be tested for edema. For example, as shown in FIG. 1, an imaging and processing device 100 can be positioned adjacent to, for example, a patient 105 lying in their hospital bed. It should be noted the imaging and processing device 100 is shown as being mounted on a tripod is shown by way of example only. In certain implementations, the imaging and processing device 100 can be a handheld device carried by, for example, a caregiver such as a nurse or doctor. In other examples, the imaging and processing device 100 can be mounted on a rolling cart or other similar easily movable structure for moving throughout, for example, a hospital, nursing home, doctor's office, or other similar locations where patients, such as patient 105, may be located in various rooms or areas.

The position of the imaging and processing device 100 relative to the patient 105 can be based upon various factors such as the illumination and image capture characteristics of the imaging and processing device 100. For example, in certain implementations, the imaging and processing device 100 may be placed less than one meter from the patient 105. In another example, the imaging and processing device 100 may be placed between 1 and 2 meters from the patient. In another example, the imaging and processing device may be placed more than 2 meters away from the patient. The actual distance between the imaging and processing device 100 an the patient 105 can also be determined based upon required reflected light or signal quality for accurately processing and detecting whether the patient currently has edema.

Figure 2:
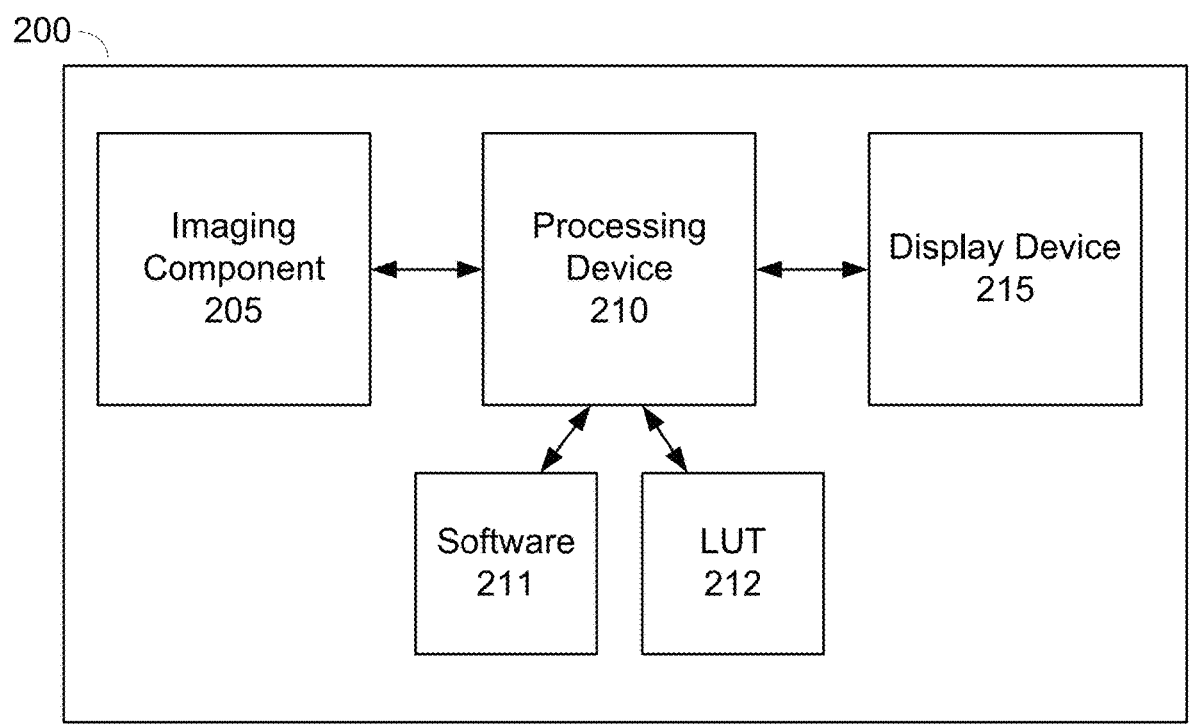
FIG. 2 depicts an illustrative imaging and processing system in accordance with one or more embodiments of the present disclosure.

FIG. 2 illustrates a sample imaging and processing system 200. In certain implementations, the imaging and processing system 200 can be incorporated into similar environments as imaging and processing device 100 as described above.

As shown in FIG. 2, the imaging and processing system 200 can include various components and/or subsystems. For example, in certain implementations, the imaging and processing system 200 can include an imagining component 205 and a processing device 210. In some embodiments, the imaging and processing system 200 can further include a display device 215 operably connected to the processing device and configured to display images and other information related to the detection of edema in a patient.

In certain implementations, the imaging component 205 can be a camera or other similar imaging device configured to capture both visible and invisible light. For example, the imaging component 205 can include a SWIR sensor, a red/blue/green (RGB) sensor, an NIR sensor, a conformal sensor, or other similar sensors configured to collect light reflected by an object and convert the collected light into a corresponding electrical signal representing data related to the collected light. The imaging component is described in greater detail in the discussion of FIG. 3 below.

As shown in FIG. 2, the imaging component 205 can be operably connected to the processing device 210. In certain implementations, the processing device 210 can be configured to receive the data relating to the collected reflected light, calculate an intensity of the reflected light, and compare the intensity of the reflected light to a control. Additionally, in various embodiments, the processing device 210 can be operably connected to the display device 215, or to another output device such as, for example, a printer, a router, other similar output devices, and combinations thereof.

In certain implementations, the processing device 210 can be configured to produce one or more images from the data received by the imaging component 205. The one or more images can be displayed, for example, on display device 215. In some embodiments, the processing device 210 can generate a single image that is displayed on the display device 215. In alternate embodiments, the processing device 210 can generate multiple images based on the data acquired from the imaging component 205.

In other implementations, the processing device 210 can include a fast switching mechanism to switch between two views (or spectral images) corresponding to spectral data collected by the imaging component 205 from two or more filters. For example, as is discussed in additional detail below in reference to FIG. 3, the imaging component can include one or more tunable filters configured to filter the collected light into wavelength bands. Thus, when a single image is displayed, the image may be generated from spectral data obtained from one filter or the spectral data from multiple filters may be combined or overlaid into a single image, which may provide increased contrast or intensity, thereby providing a comparison of the overlaid images. In other embodiments, separate images corresponding with the data obtained from each filter may be displayed side-by-side.

In some embodiments, the processing device 210 can be in communication with one or more non-transitory, computer-readable storage mediums. For example, the processing device 210 may be configured to access a first computer readable storage medium to access various software 211 configured to provide instructions to the processing device. The instructions, when executed, can cause the processing device to perform various functions such as the edema detection processes as described herein.

The processing device may further be configured to access a second computer readable medium that contains a look-up table 212 ("LUT"). In certain implementations, the LUT 212 can include information that, when accessed by the processing device 210, enables the processing device to tune the one or more filters of the imaging component 205 to detect edema in certain tissue. For example, the LUT 212 may include a number of voltages that, when applied to a filter, enable the filter to produce filtered light of a spectral shape associated with one or more tissue types related to various degrees of edema. In the case of a multi-stage filter, the LUT 212 can include voltages that can be applied to each stage of the filter in order to produce filtered light associated with tissue types related to various degrees of edema.

In certain implementations, the processing device 210 can be configured to acquire the appropriate information from the LUT 212 based on user input or image processing. The processing device 210 can then communicate this information to a controller of the imaging component 205, which in turn applies the appropriate voltages to each filter or each stage in each filter. In some embodiments, this process may occur in real time or in near real time providing flexibility for detecting multiple tissue types of interest in near real time. This may allow the user to modify or completely change the displayed image while the intraoperative optical diagnostic device is in use.

It should be noted that, while the software 211 and LUT 212 are shown as being in separate computer readable mediums, this is provided by way of example only. Depending upon the resources available and the design of the imaging and processing system 200, the software 211 and LUT 212 can be implemented on a single computer readable medium. However, in certain implementations, the LUT 212 can be stored at a remote location accessible to the processing device 210 via, for example, wired or wireless network communications. In such an arrangement, the LUT 212 can be updated at a central location (e.g., a manufacturer of the imaging and processing device's server), and all imaging and processing devices 200 currently operating can access the updated LUT 212 from the central location.

Figure 3:
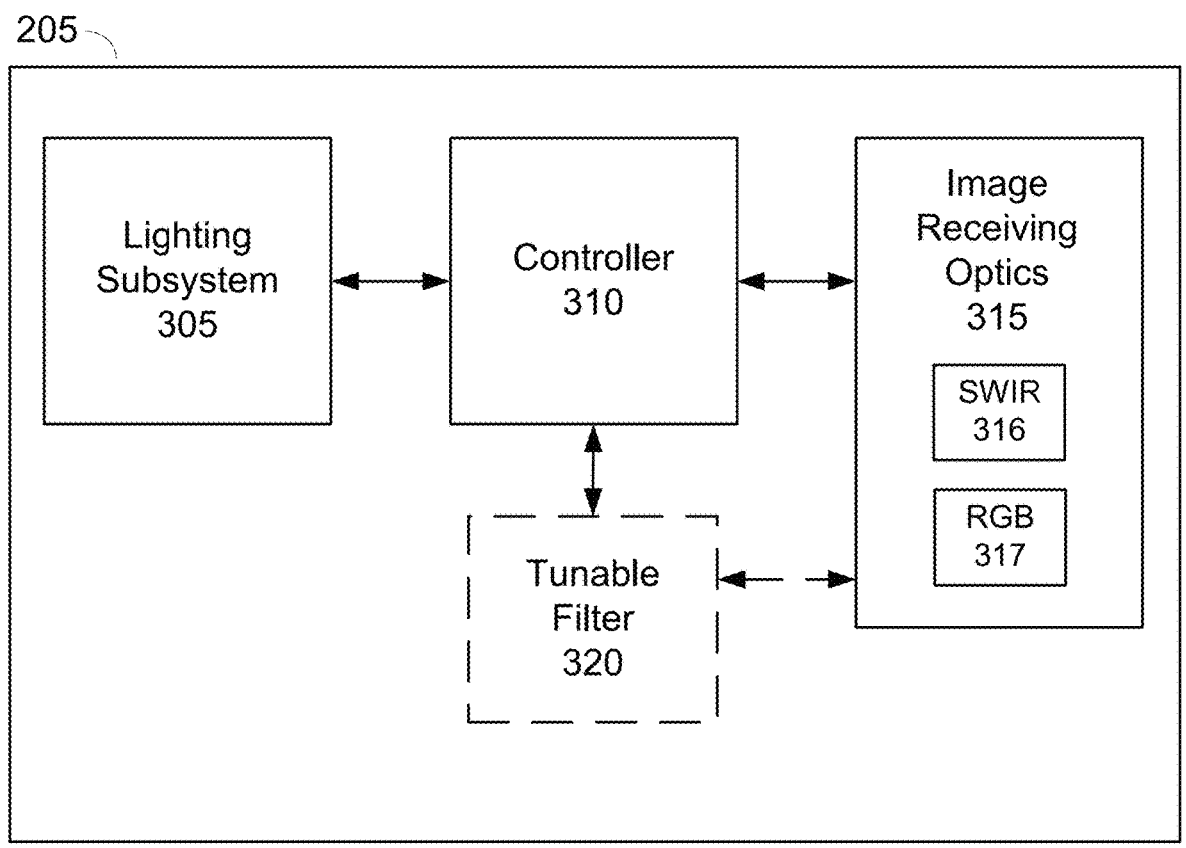
FIG. 3 depicts an illustrative imaging device in accordance with one or more embodiments of the present disclosure.

FIG. 3 illustrates a sample architecture for the imagining component 205 as described above in FIG. 2. As shown in FIG. 3, the imaging component 205 can include various additional components and subsystems. For example, the imaging component 205 can include a controller 310 operably connected to, and configured to control, a lighting subsystem 305, imaging receiving optics 315, and an optional filter 320. It should be noted that, as shown in FIG. 3, the filter 320 is shown as an optional component. As described below in additional detail, depending upon the implantation of the imaging component 205, and the functionality of the various components incorporate there, the functionality of the filter 320 can be incorporated into an additional component such as, for example, the image receiving optics 315.

Referring again to FIG. 3, the controller 310 can be implemented as a processing device configured to execute a set of instructions related to operation of the imaging and processing device 205 and the various components integrated therein. The instructions can be stored on a computer readable medium operably connected to the controller 310 (not shown in FIG. 3). In certain implementations, the controller 310 can be a dedicated processing device programmed specifically for controlling the various components of the imaging and processing system 205. In such an arrangement, the instructions related to operating the controller 310 can be included on a computer-readable medium integrated directly into the controller 310.

In certain implementations, the lighting subsystem 305 can be configured to irradiate tissue being imaged using an integrated light source such as, for example, a laser illumination source, a broadband light source, and/or an ambient light source. In some embodiments, the light source may be an independent element (e.g., remotely connected) to the imaging and processing device 205 for carrying out the methods described above. In other embodiments, the light source may be integrated with the imaging and processing device 205.

In some embodiments, the lighting subsystem 305 can include filters on one or more light sources. For example, in certain embodiments, an infrared (IR) long pass filter can be included on a light source to eliminate visible light emitted from the light source. IR light is eye safe and invisible to visible sensors.

In certain implementations, the image receiving optics 315 can be configured to collect light reflected by the irradiated tissue. In certain implementations, the image receiving optics 315 can include an image detector such as, for example, a SWIR detector 316 and/or a RGB detector 317. In alternate implementations, the image receiving optics 315 can also include charge-coupled device (CCD) detectors or complementary metal-oxide semiconductor (CMOS) detectors, which are typically used to collect visible light for photographs and/or with Raman spectroscopic imaging systems, or indium gallium arsenide (InGaAs) or focal plane array (FPA) detectors, which are typically used in near-infrared spectroscopic imaging systems.

In certain implementations, additional NIR and SWIR cameras and/or detectors can be incorporated into the image receiving optics. For example, the image receiving optics can further include a mercury cadmium telluride (MCT) IR detector, an Indium Antimonide (InSb) IR detector or photodiode, a quantum dot camera, and/or other similar NIR and SWIR cameras and detectors.

In certain embodiments, the imaging receiving optics 315 can include optics for focusing light collected from the tissue. For example, in some embodiments, the imaging receiving optics 315 can include telescopic or other similar focusing optics configured for at least one of locating and focusing on tissue and/or collecting light from the tissue.

As noted above, the imaging and processing device 205 can further include a filter 320 configured to filter collected light information as received by the image receiving optics 315. In certain implementations, the filter 320 can include any tunable filter known in the art including, but not limited to, SWIR multi-conjugate liquid crystal tunable filters, SWIR liquid crystal tunable filters, Fabry Perot angle tuned filters, acousto-optic tunable filters, liquid crystal tunable filters, Lyot filters, Evans split element liquid crystal tunable filters, Solc liquid crystal tunable filters, fixed wavelength Fabry Perot tunable filters, air-tuned Fabry Perot tunable filters, mechanically-tuned Fabry Perot tunable filters, and liquid crystal Fabry Perot tunable filters. In certain embodiments, the filter 320 can be a multi-conjugate liquid crystal tunable filter (MCF). A MCF includes a series of stages composed of polarizers, retarders, and liquid crystals. As a result of this arrangement, the MCF is capable of providing diffraction limited spatial resolution and spectral resolution consistent with a single stage dispersive monochromator. The MCF may be tuned to any wavelength in the given filter range. In some embodiments, the MCF may be controlled by a processor.

In certain implementations, the filter 320 can be implemented as a fixed filter array. For example, when processing the collected light using a snapshot imaging spectrometer, a fixed filter array can be used for preprocessing of the collected light prior to passing to the spectrometer for analysis.

In additional embodiments, the filter 320 can be a multivariate optical element filter. In certain embodiments, the filter may be a conformal filter. The term "conformal filter" generally refers to filters that simultaneously transmit multiple passbands, i.e., spectral shapes. The use of conformal filters can improve discrimination performance by, for example, discriminating between a target and background and increasing the throughput of a tunable filter, thereby, improving the speed of an analysis. Conformal filters can be tunable to enable tuning to a variety of different configurations. Examples of tunable filters that can be configured for use as a conformal filter include, but are not limited to, a liquid crystal tunable filter, an acoustic optical tunable filter, a Lyot liquid crystal tunable filter, an Evans Split-Element liquid crystal tunable filter, a Solc liquid crystal tunable filter, a ferroelectric liquid crystal tunable filter, a Fabry Perot liquid crystal tunable filter, and combinations thereof.

In additional implementations, the imaging and processing device 205 can be implemented as a dual polarization device. In such an implementation, the imaging and processing device 205 can include an optical separator positioned to receive light reflected from the tissue and separating the reflected light into two or more optical paths. It should be noted that, although such a device can include more than two optical paths, for simplicity such embodiments are referred to as "dual polarization" devices. Each optical path can include one or more filters that reflect light of particular wavelengths removing them from the optical path and allowing other light to pass through the filter generating filtered light, i.e. a "filtered component." The one or more filters can be any of the tunable filters or conformal filters such as those described above. In some embodiments, each optical path can terminate at a detector which is positioned to receive and detect the filtered component. In other embodiments, a single detector may be positioned to simultaneously receive and detect the filtered components from each optical path. Thus, embodiments may include one or more detectors depending on the configuration. The imaging and processing devices of such embodiments, including one or more detectors, may further include a processor electronically connected to the one or more detectors that receive data from the detector. The processor may be configured to analyze the data and generate an image as disclosed herein.

It should be noted that the included components and their relative arrangement, as is described above in FIG. 3 is provided by way of example only. Depending upon the design and intended functionality of the imaging and processing device 205, the components contained therein, and their arrangement, may vary accordingly.

Figure 4:
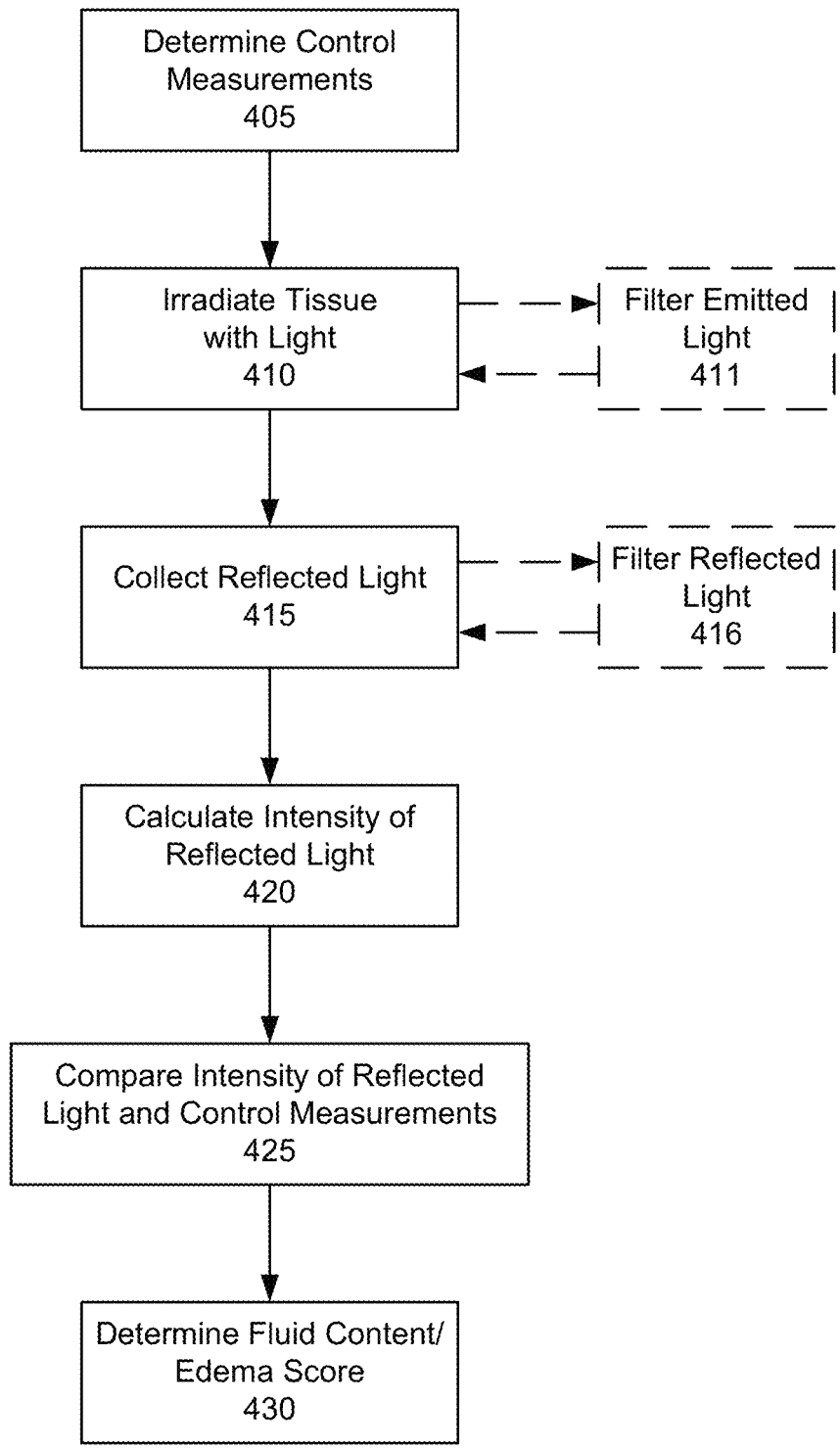
FIG. 4 depicts a sample flowchart illustrating a process for determining a likelihood of a patient having edema in accordance with one or more embodiments of the present disclosure.

FIG. 4 illustrates a sample process for detecting whether a patient is experiencing edema. Initially, a processing device such as processing device 210 as described above, can determine 405 control measurements for the patient. For example, as noted above, the control measurements can be determined 405 by collecting reflected light from unaffected tissue of the patient such as, for example, tissue of the upper arm, thigh, or back, or the control measurements can be determined from an unaffected subject or collection of subjects. For example, in some embodiments, control measurements may be an average absorbance obtained from limbs, hands, feet, ankles, calves, abdomen, or combinations thereof from numerous unaffected subjects.

After control measurements are determined 405, the process can advance to detecting whether the patient is currently exhibiting symptoms of edema. A device, such as imaging and processing device 205 as described above, can irradiate 410 the patient's tissue with light. In certain implementations, irradiating 410 the tissue can be carried out using ambient light or a light source such as, for example, a laser illumination source, a broadband light source, and an ambient light source as described above. Depending upon the implementation of the light source, the process can optionally include filtering 411 the emitted light. For example, in some examples, the process can include filtering 411 the illuminating light by, for example, removing visible spectrum light.

A detection device, such as image receiving optics 315 as described above, can be configured to collect 415 the light reflected by the patient's tissue. Thus, in various embodiments, collecting 415 the reflected light can be carried out by an image detector such as, for example, CCD detectors or CMOS detectors, which are typically used to collect visible light for photographs and with Raman spectroscopic imaging systems, and/or InGaAs or focal plane array FPA detectors, which are typically used in near-infrared spectroscopic imaging systems that is an independent element of devices for carrying out the methods described above or the image detector can be associated with a light source.

Depending upon the conditions under which the reflected light is collected 415, and the intended processing of the collected light, the collected light can optionally be filtered 416. For example, the reflected light can be filtered 416 into one or more wavelength bands to produce hyperspectral images.

A processing device, such as processing device 210 as described above, can be configured to receive information related to the collected reflected light and calculate 420 the intensity of the collected reflected light. In certain implementations, the processing device can calculate 420 the intensity of collected reflected light having wavelengths of about 900 nm to about 1300 nm, about 1400 nm to about 1550 nm, or combinations thereof, or any individual wavelength or range encompassed by these ranges. For example, in some embodiments, the processing device may calculate 420 an intensity of reflected light having a wavelength of about 700 nm to about 1100 nm, about 1100 nm to about 1300 nm, about 1200 nm to about 1300 nm, about 1100 nm to about 1250 nm, about 900 nm to about 1100 nm, about 900 nm to about 1150 nm, and/or the like.

The processing device can be further configured to compare 425 the intensity of the reflected light to the control measurements. Changes in absorption of light of these wavelengths can be indicative of edema. As such, by comparing 425 the intensity of the reflected light and control measurements, the processing device can determine 430 a fluid content and/or an edema score for the patient. As used herein, an edema score refers to the likelihood that a patient is currently experiencing edema. An edema score may also provide a quantified reading of the severity of the edema. For example, the edema score can be a number ranging from 0.0 to 1.0. A reading of 0.0 can represent the control measurement of the patient's normalized tissue. In certain implementations, a larger edema may represent more severe edema. Thus, the process as described above in regard to FIG. 4 can be used to identify a disease or condition associated with edema.

Figure 5:
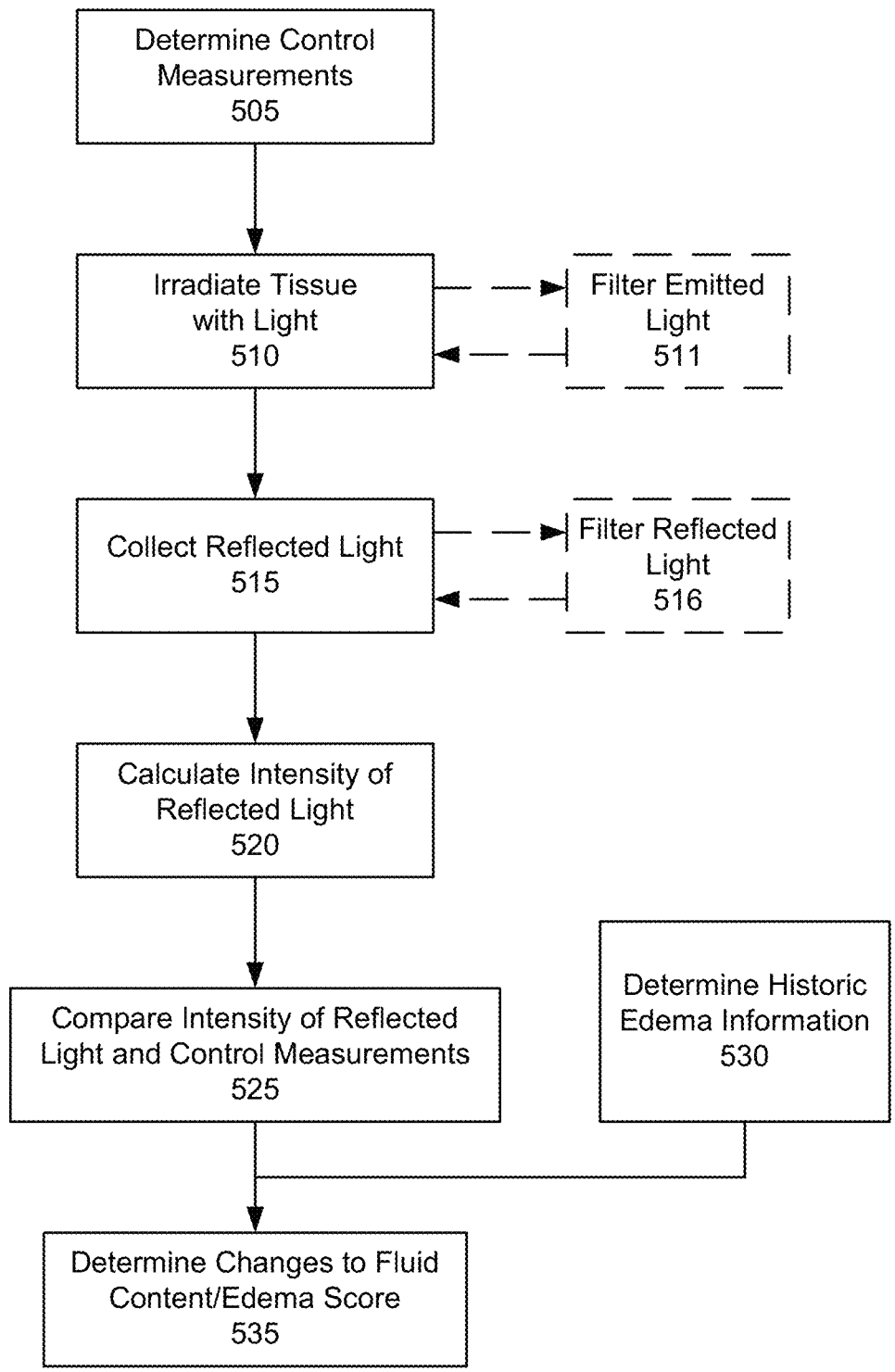
FIG. 5 depicts a sample flowchart illustrating a process for monitoring a patient's edema levels in accordance with one or more embodiments of the present disclosure.

In addition to identifying a disease or condition associated with edema, the processes and techniques as taught herein can further be used to monitor a patient that has been previously identified as having peripheral edema. For example, FIG. 5 illustrates a sample process for detecting and monitoring changes in a patient's edema. Initially, a processing device such as processing device 210 as described above, can determine 505 control measurements for the patient. For example, as noted above, the control measurements be determined 505 by collecting reflected light from unaffected tissue of the patient such as, for example, tissue of the upper arm, thigh, or back, or the control measurements can be determined from an unaffected subject or collection of subjects.

After the control measurements are determined 505, the process can advance to detecting a current edema level or score for the patient. A device, such as imaging and processing device 205 as described above, can irradiate 510 the patient's tissue with light. Depending upon the implementation of the light source, the process can optionally include filtering 511 the emitted light. For example, in some examples, the process can include filtering 511 the illuminating light by, for example, removing visible spectrum light.

A detection device, such as image receiving optics 315 as described above, can be configured to collect 515 the light reflected by the patient's tissue. Depending upon the conditions under which the reflected light is collected 515 and the intended processing of the collected light, the collected light can optionally be filtered 516. For example, the reflected light can be filtered 516 into one or more wavelength bands to produce hyperspectral images.

A processing device, such as processing device 210 as described above, can be configured to receive information related to the collected reflected light and calculate 520 the intensity of the collected reflected light. The processing device can be further configured to compare 525 the intensity of the collected reflected light to the control measurements to determine a current edema score for the patient.

The processing device can also determine 530 a patient's historic edema information. The historic information can include, for example, data retreived from the patient's medical record or other similar information related to, in this example, previous edema measurements, levels, or scores. For example, the patient's edema score as determined in the process described with regard to FIG. 4 above can be stored in the patient's medical record. The processing device can then determine 530 the previous edema score from the medical record.

The processing device can compare the current edema score for the patient against the patient's historic edema information to determine 535 any changes to the patient's edema level or score. Such changes can be indicative of changes to the patient's fluid content and/or a changing, worsening, or improving medical condition. A caregiver such as the patient's physician can review the changes in the patient's edema scores or levels and adjust the patient's treatment regimen accordingly.

Figure 6:
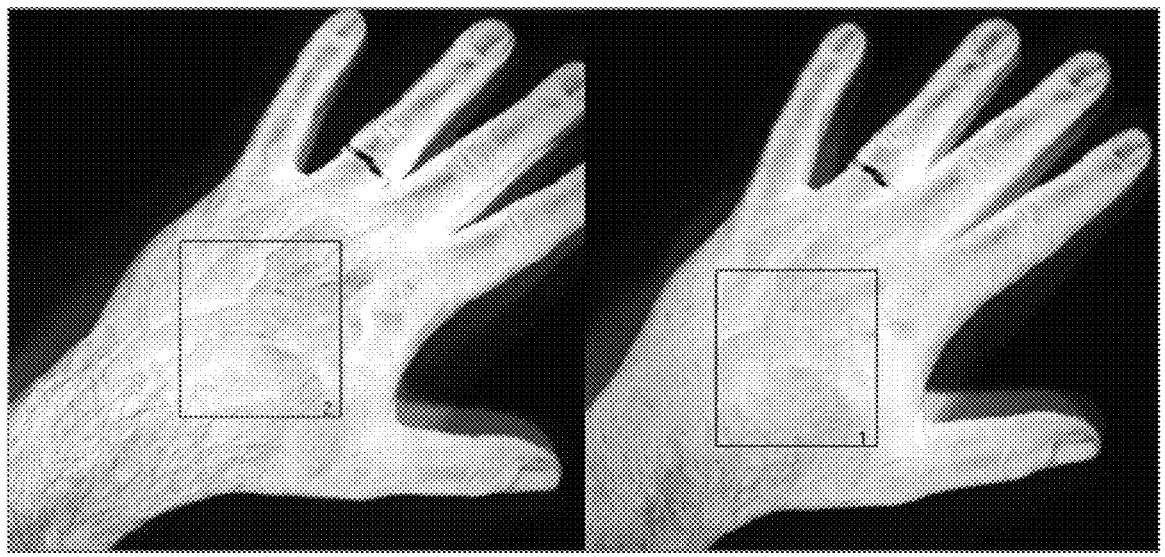
FIG. 6 depicts a sample comparison image of a patient's hand in accordance with one or more embodiments of the present disclosure.
Figure 7:
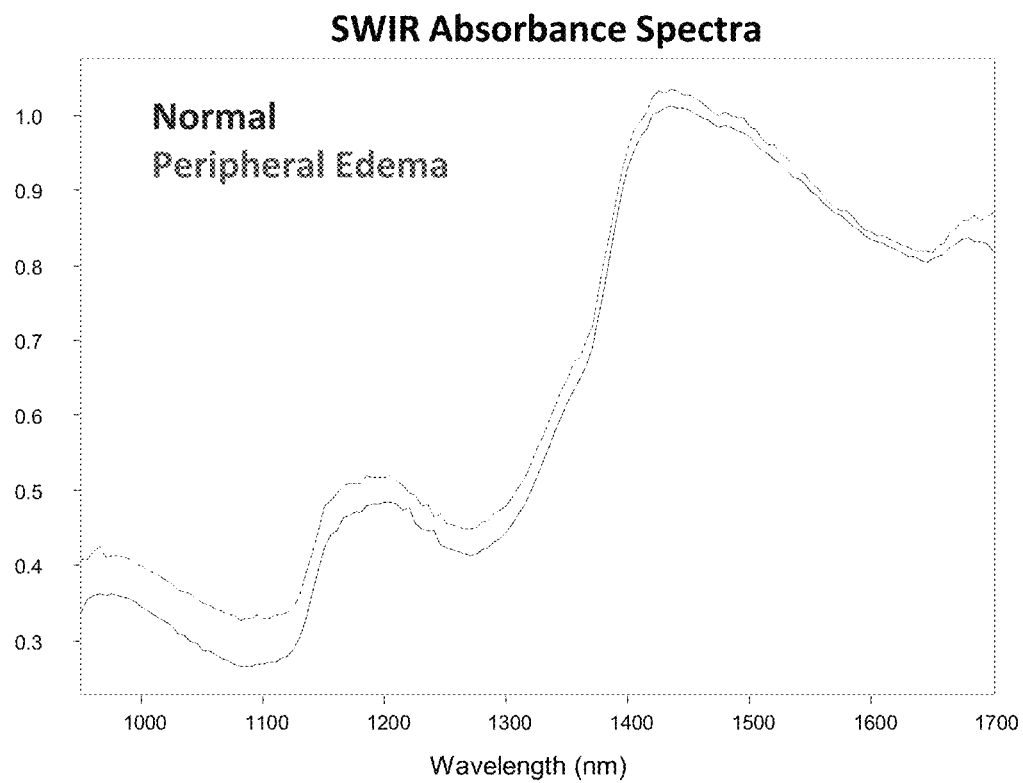
FIG. 7 depicts a sample absorption spectra for a patient's hand in accordance with one or more embodiments of the present disclosure.

FIGS. 6 and 7 illustrate sample output images and data that can be produced for further analysis and/or review using the techniques, systems, and processes as described herein. For example, FIG. 6 illustrates a set of images of a patient's hand. On the left, the image represents normal tissue. In the normal image, the subcutaneous vasculature is highly visible. However, in the right image, the patient is experiencing peripheral edema. Due to the increased water content in the patient's tissue, the vasculature contrast decreases and, as such, the measured calculated intensity of the reflected light will reflect this decrease in vasculature contrast. FIG. 7 illustrates a comparison of the SWIR absorption spectra for normal tissue and tissue exhibiting signs of peripheral edema.

In addition to detecting disease conditions, exercise-related edema can be detected by increased adsorption of light having wavelengths in the range of about 900 nm to about 1300 nm and about 1400 nm to about 1550 nm, when absorption spectra of the hand of an individual pre-workout and post-workout are compared. Accordingly, even mild edema, like exercise-induced edema, can be detected based on the change in intensity of reflected light at these wavelengths. The method of the embodiments described above are therefore applicable for identifying any condition associated with edema, not necessarily only those caused by disease or other malady.

It should be noted that the implementation details as described above are provided by way of example only. For example, the image acquisition system and environment as shown in FIG. 1 is provided for illustrative purposes only. Based upon the computation requirements of the processing device and the imaging characteristics of an image capture device, the systems, methods and processes as described herein can be incorporated into various devices and systems. For example, the system for detecting edema as described and taught herein can be realized using a smart phone having a light source and an image detector. The smart phone may have an installed program or app for calculating intensity of light at wavelengths in the range of about 900 nm to about 1300 nm and about 1400 nm to about 1550 nm, or any of the ranges defined above. In particular, the program or app may calculate the intensity of collected light at wavelengths of about 700 nm to about 1100 nm. The smartphone can be configured to transmit information related to the calculated intensity of the collected light to a remote location such as a physician's office or other similar caregiver. The transmitted information can be used to remotely monitor any changes in the patient's peripheral edema and, if necessary, make treatment changes such as, for example, diet changes, medication changes, exercise recommendations, and other similar changes.

Such systems involving smart phones may be particularly useful for detecting edema associated with heart disease and exercise quickly and with a device that a large portion of the population already owns and uses regularly. Rather than teaching a heart failure patient to use a completely new device, or subject the patient to regular testing at a clinician's office, hospital, or other similar location, the patient can learn to use their personal smartphone, or other similar imaging and processing device, to measure their current edema score according to the processes and techniques as described herein.

In other examples, the system for detecting edema as described herein can be implemented in, for example, a medical device. In some embodiments, the system may be a spectroscopic imaging device. In such embodiments, spectroscopic imaging may be used to obtain control information from unaffected tissue, such as the upper arm, thigh, or back of the subject and affected or potentially affected tissue at, for example, the foot, ankle, calf, or hand of the subject. In some embodiments, the spectroscopic imaging device may include a tunable filter to filter light into one or more wavelength bands. The bands can then be detected using a spectroscopic imaging device to thereby generate a hyperspectral image. Thus, the method of some embodiments may include separating the reflected light into wavelength bands and generating a hyperspectral image. Such methods may further include overlaying or fusing hyperspectral images and, in some embodiments, overlaying or fusing hyperspectral images with visible images to spatially resolve individual pixels in the hyperspectral image.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for detecting edema in a patient, the system comprising:
   a light source configured to irradiate a patient's tissue with light;
   a tunable filter configured to filter light reflected from the patient's tissue into one or more wavelength bands;
   a detector configured to collect the tuned reflected light and generate data associated with the tuned reflected light;
   a computer readable medium;
   a processing device operably connected to the detector and the computer readable medium and configured to:
      receive the data associated with the tuned reflected light that is separated light into one or more wavelength bands;
      generate a visible image and a hyperspectral image,
      calculate the intensity of the tuned reflected light,
      compare the calculated intensity of the tuned reflected light against a control measurement;
      fuse intensity data from the visible image and the hyperspectral image to spatially resolve individual pixels in the hyperspectral image,
      determine whether the patient's tissue exhibits symptoms of edema,
      access the computer readable medium, wherein the computer readable medium contains a look up table (LUT) that includes a plurality of voltages that, when applied to a filter, enable the filter to produce filtered light of a spectral shape associated with one or more tissue types related to edema, and
      determine an edema score for the patient, wherein the edema score represents at least one of whether the patient has edema and a severity of the patient's edema; and
   a display device operably connected to the processing device and configured to display images and information related to the detection of edema in the patient,
   wherein the detector comprises one of an indium gallium arsenide detector and a focal plane array detector.

2. The system of claim 1, wherein the processing device is further configured to determine a control measurement for a control sample.

3. The system of claim 1, wherein the at least one filter is at least one of a shortwave infrared tunable filter, a Fabry Perot tunable filter, a multi-conjugate crystal tunable filter, and a conformal filter.

4. The system of claim 1, further comprising a plurality of tunable filters.

5. The system of claim 4, wherein the plurality of tunable filters are configured to filter the reflected light to wavelength ranges of at least one of 900 nm to 1100 nm, 1150 nm to 1300 nm, and 1400 nm to 1550 nm.

6. The system of claim 1, wherein the light source comprises at least one of a laser illumination source, a broadband light source, and an ambient light source.

7. A method for detecting edema in a patient, the method comprising:
   irradiating, by a light source, a patient's tissue with light;
   filtering, by a tunable filter, light reflected from the patient's tissue into one or more wavelength bands;
   collecting, by a detector, the tuned reflected light from the patient's tissue;
   generating, by the detector, data associated with the tuned reflected light;
   receiving, by a processing device operably connected to the detector, the tuned reflected light that is separated light into one or more wavelength bands;
   generating, by the processing device, a visible image and a hyperspectral image;
   calculating, by the processing device, the intensity of the tuned reflected light;
   comparing, by the processing device, the calculated intensity of the tuned reflected light against a control measurement;
   fusing, by the processing device, intensity data from the visible image and the hyperspectral image to spatially resolve individual pixels in the hyperspectral image;
   determining, by the processing device, whether the patient's tissue exhibits symptoms of edema;
   accessing, by the processing device, a look up table (LUT) that includes a plurality of voltages that, when applied to a filter, enable the filter to produce filtered light of a spectral shape associated with one or more tissue types related to edema;
   determining, by the processing device, an edema score for the patient, wherein the edema score represents at least one of whether the patient has edema and a severity of the patient's edema; and
   displaying, by a display device operably connected to the processing device, images and information related to the detection of edema in the patient,
   wherein the detector comprises one of an indium gallium arsenide detector and a focal plane array detector.

8. The method of claim 7, further comprising determining, by the processing device, a control measurement for a control sample.

9. The method of claim 7, wherein the at least one filter is at least one of a shortwave infrared tunable filter, a Fabry Perot tunable filter, a multi-conjugate crystal tunable filter, and a conformal filter.

10. The method of claim 7, further comprising filtering, by the tunable filter, the reflected light to wavelength ranges of at least one of 900 nm to 1100 nm, 1150 nm to 1300 nm, and 1400 nm to 1550 nm.

11. The method of claim 7, wherein the light source comprises at least one of a laser illumination source, a broadband light source, and an ambient light source.

* * * * *